United States Patent [19]

Das

[11] Patent Number: 4,609,671
[45] Date of Patent: Sep. 2, 1986

[54] 5,6-EPOXY-7-OXABICYCLOHEPTANE SUBSTITUTED AMINO PROSTAGLANDIN ANALOGS USEFUL IN THE TREATMENT OF THROMBOTIC DISEASE

[75] Inventor: Jagabandhu Das, Plainsboro, N.J.

[73] Assignee: E. R. Squibb & Sons, Inc., Princeton, N.J.

[21] Appl. No.: 749,232

[22] Filed: Jun. 27, 1985

[51] Int. Cl.$^4$ ................. A61K 31/335; A61K 31/557; C07D 307/00
[52] U.S. Cl. .................................. 514/468; 549/459
[58] Field of Search ......................... 549/459; 514/468

[56] References Cited

U.S. PATENT DOCUMENTS

| | | | |
|---|---|---|---|
| 4,143,054 | 3/1979 | Sprague | 549/463 |
| 4,187,236 | 2/1980 | Sprague | 549/463 |
| 4,220,594 | 9/1980 | Sprague | 549/463 |
| 4,228,180 | 10/1980 | Sprague | 549/463 |
| 4,254,044 | 3/1981 | Sprague | 549/463 |
| 4,416,896 | 11/1983 | Nakane | 549/463 |
| 4,456,617 | 6/1984 | Nakane | 549/463 |

FOREIGN PATENT DOCUMENTS 0043292 8/1982 European Pat. Off. .
2039909 8/1980 United Kingdom .

Primary Examiner—Henry R. Jiles
Assistant Examiner—Bernard I. Dentz

Attorney, Agent, or Firm—Lawrence S. Levinson; Burton Rodney

[57] ABSTRACT 5-6-Epoxy-7-oxabicycloheptane substituted amino prostaglandin analogs are provided having the structural formula

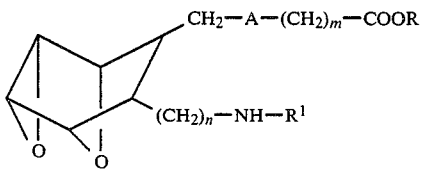

wherein A is CH=CH or $(CH_2)_2$, m is 1 to 8, n is 0 to 5, R is H, lower alkyl, alkali metal or hydroxylamine salt, and $R^1$ is lower alkyl, aryl, aralkyl, cycloalkyl, cycloalkylalkyl, lower alkenyl, lower alkoxy, aralkoxy or

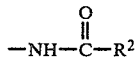

including all stereoisomers thereof.

The compounds are cardiovascular agents useful, for example, in the treatment of thrombotic disease.

12 Claims, No Drawings

5,6-EPOXY-7-OXABICYCLOHEPTANE SUBSTITUTED AMINO PROSTAGLANDIN ANALOGS USEFUL IN THE TREATMENT OF THROMBOTIC DISEASE

DESCRIPTION OF THE INVENTION

The present invention relates to 5,6-epoxy-7-oxabicycloheptane substituted amino prostaglandin analogs which are cardiovascular agents useful, for example, in the treatment of thrombotic disease. These compounds have the structural formula

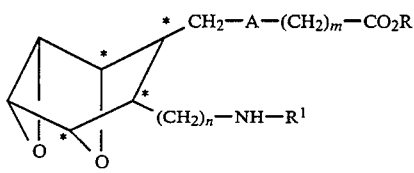 I and including all stereoisomers thereof, wherein A is $CH=CH$ or $(CH_2)_2$; m is 1 to 8; n is 0 to 5; R is hydrogen, lower alkyl, alkali metl salt or polyhydroxylamine salt; and $R^1$ is lower alkyl, aryl, aralkyl, cycloalkyl, cycloalkylalkyl, lower alkenyl, lower alkoxy, aralkoxy or

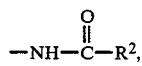

wherein $R^2$ is lower alkyl, aryl, aralkyl, lower alkoxy, aryloxy, aralkoxy, lower alkylamino, arylamino or aralkylamino.

The term "lower alkyl" or "alkyl" as employed herein by itself or as part of another group includes both straight and branched chain radicals of up to 12 carbons, preferably 1 to 8 carbons, such as methyl, ethyl, propyl, isopropyl, butyl, t-butyl, isobutyl, pentyl, hexyl, heptyl, 4,4-dimethylpentyl, octyl, 2,2,4-trimethylpentyl, nonyl, decyl, undecyl, dodecyl, the various branched chain isomers thereof, and the like as well as such groups including a halo-substituent, such as F, Br, Cl or I or $CF_3$, an alkoxy substituent, an aryl substituent, an alkyl-aryl substituent, a haloaryl substituent, a cycloalkyl substituent, an alkylcycloalkyl substituent, hydroxy, an alkylamino substituent, or an alkylthio substituent.

The term "cycloalkyl" by itself or as part of another group includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl, any of which groups may be substituted with 1 or 2 halogens, 1 or 2 lower alkyl groups and/or lower alkoxy groups, an aryl group, 1 or 2 hydroxy groups, 1 or 2 alkylamino groups, or 1 or 2 alkylthio groups.

The term "aryl" or "Ar" as employed herein by itself or as part of another group refers to monocyclic or bicyclic aromatic groups containing from 6 to 10 carbons in the ring portion, such as phenyl, naphthyl, substituted phenyl or substituted naphthyl wherein the substituent on either the phenyl or naphthyl may be 1 or 2 lower alkyl groups, 1 or 2 halogens (Cl, Br or F), 1 or 2 lower alkoxy groups, 1 or 2 hydroxy groups, 1 or 2 alkylamino groups, or 1 or 2 alkylthio groups. Phenyl may also be independently substituted with an amino, a

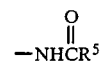

or a thiol group.

The term "aralkyl", "aryl-alkyl" or "aryl-lower alkyl" as used herein by itself or as part of another group refers to lower alkyl groups as discussed above having an aryl substituent, such as benzyl.

The term "lower alkenyl" or "alkenyl" includes straight or branched chain radicals of from 2 to 12 carbons, preferably 2 to 6 carbons in the normal chain, which include one double bond in the normal chain, such as ethenyl, 2-propenyl, 3-butenyl, 2-butenyl, 1-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl and the like.

The term "lower alkoxy", "alkoxy" or "aralkoxy" includes any of the above lower alkyl, alkyl or aralkyl groups linked to an oxygen atom.

The term "halogen" or "halo" as used herein refers to chlorine, bromine, fluorine or iodine with chlorine being preferred.

The term "polyhydroxylamine" refers to glucamine salt, tris(hydroxymethyl)aminomethane salt and the like.

The term "halogen" or "halo" as used herein by itself or as part of another group refers to chlorine, bromine, fluorine or iodine with chlorine being preferred.

The terms "$(CH_2)_m$" and "$(CH_2)_n$" include a straight or branched chain radicals having from 1 to 8 carbons in the normal chain in the case of "$(CH_2)_m$" and 1 to 5 carbons in the normal chain in the case of "$(CH_2)_n$" and may contain one or more lower alkyl substituents. Examples of $(CH_2)_m$ and $(CH_2)_n$ groups include

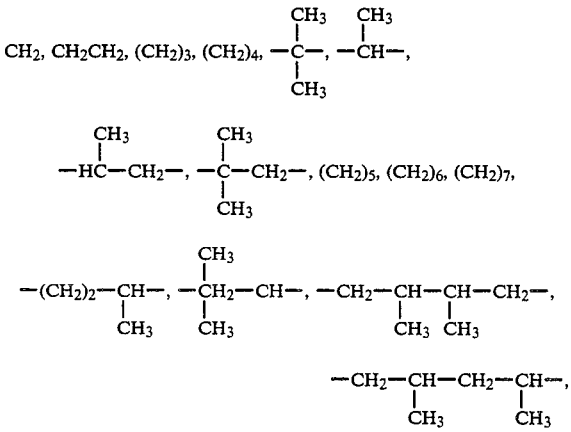

and the like.

Preferred are those compounds of formula I wherein A is $CH=CH$, m is 2 to 4, R is H, n is 0 or 1, and $R^1$ is phenyloxy, pentyloxy, pentyl, hexyl or heptyl, or

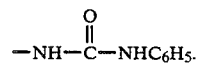

The various compounds of the invention may be prepared as outlined below.

Dione having the structure A

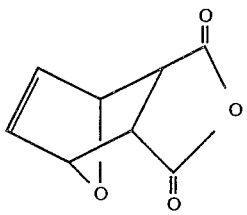

A that is, 7-oxabicyclo[2.2.1]-5-heptene-2,3-dicarboxylic anhydride [Ber. 62, 554 (1920); Ann. 460, 98 (1928)]is reduced, for example, by reacting with lithium aluminum hydride or diisobutyl aluminum hydride in the presence of an inert organic solvent such as tetrahydrofuran, ether or toluene at reduced temperatures of from about −78° C. to about 67° C. to form diol B of the structure

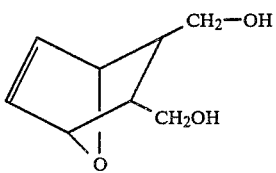

B

The diol B is subjected to a chloroformylation reaction by reacting B dissolved in an inert organic solvent as described above, with phosgene in the presence of a solvent such as tetrahydrofuran, toluene, benzene or xylene, to form an alcohol of the structure

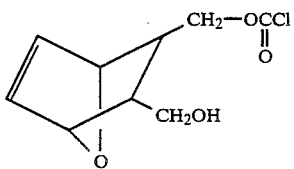

C

The alcohol C is dissolved in an inert organic solvent such as methylene chloride, tetrahydrofuran or ether and then reacted with an organic base, such as pyridine, triethylamine, N,N-dimethylaminopyridine or diazabicycloundecane (DBU) at reduced temperatures of from about −78° C. to about 25° C., to form cyclic carbonate D

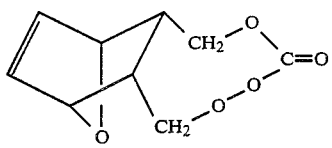

D

The cyclic carbonate D is then subjected to alcoholysis by reacting D with an alkanol (alkyl-OH) having from 1 to 12 carbons, such as ethanol, n-propanol, isopropanol, butanol, pentanol, hexanol, heptanol, octanol, nonenol or decanol, including all the various isomers thereof, preferably isopropyl alcohol, employing a molar ratio of D alkanol of within the range of from about 1:10 to about 1:100 to form hydroxycarbonate E

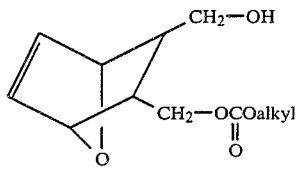

E (wherein alkyl contains 1 to 12 carbons as defined herein).

Thereafter, the hydroxy carbonate E is tosylated (or otherwise protected) by reacting E (dissolved in methylene chloride, and a basic solvent such as pyridine, triethylamine or dimethylaminopyridine) with tosyl chloride or other protecting agent, such as methane sulfonyl chloride (mesyl chloride) and trifluoromethanesulfonic anhydride, to form the tosylate F or other protected compound

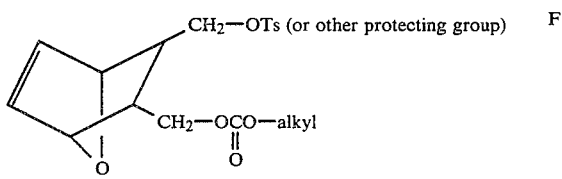

F

Then, the tosylate F dissolved in an inert solvent such as dimethylsulfoxide, or dimethylformamide is cyanated by reacting F with an alkali metal cyanide such as NaCN or KCN employing a molar ratio of IV:cyanide of within the range of from about 1:1 to about 10:1, at elevated temperatures of from about 80° C. to about 130° C., in an inert atmosphere, such as an argon atmosphere, to form the cyanocarbonate G (which itself is a new compound)

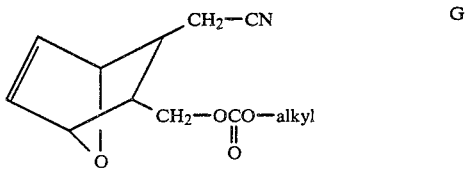

G

Cyanocarbonate G is dissolved in an alcohol such as methanol or ethanol and treated with aqueous alkali metal carbonate such as potassium carbonate at reduced temperature to form cyano-alcohol H

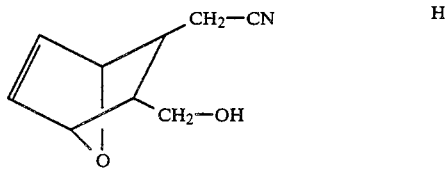

H which is made to undergo tetrahydropyranyl ether formation by reacting cyano alcohol H with dihydropyran in the presence of an inert organic solvent such as methylene chloride or ether and catalytic amount of p-toluene sulfonic acid at reduced temperatures of from about 0° C. to about 10° C., to form the tetrahydropyranyl ether of formula J

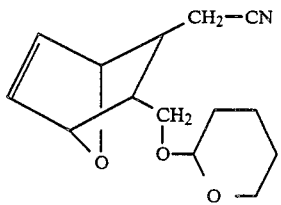

J

Compound J is then made to undergo epoxide formation by treating a solution of J in methylene chloride or other appropriate solvent with m-chloroperoxybenzoic acid at reduced temperatures to form epoxy nitrile II (which itself is a novel compound)

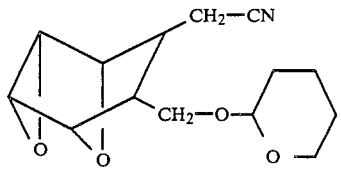

II (which is a novel compound). The compounds of formula I of the invention may be formed starting with compound II in accordance with the following reaction sequence.

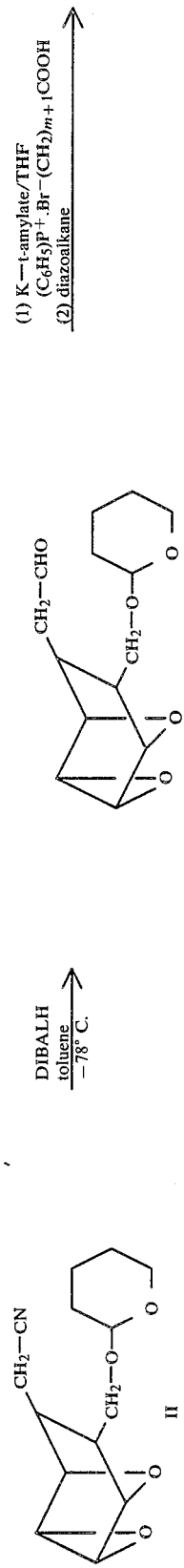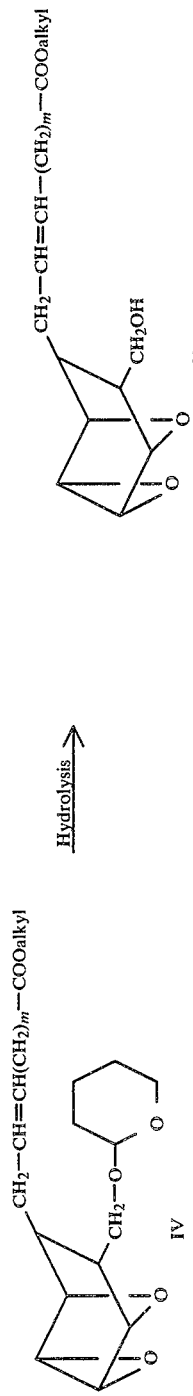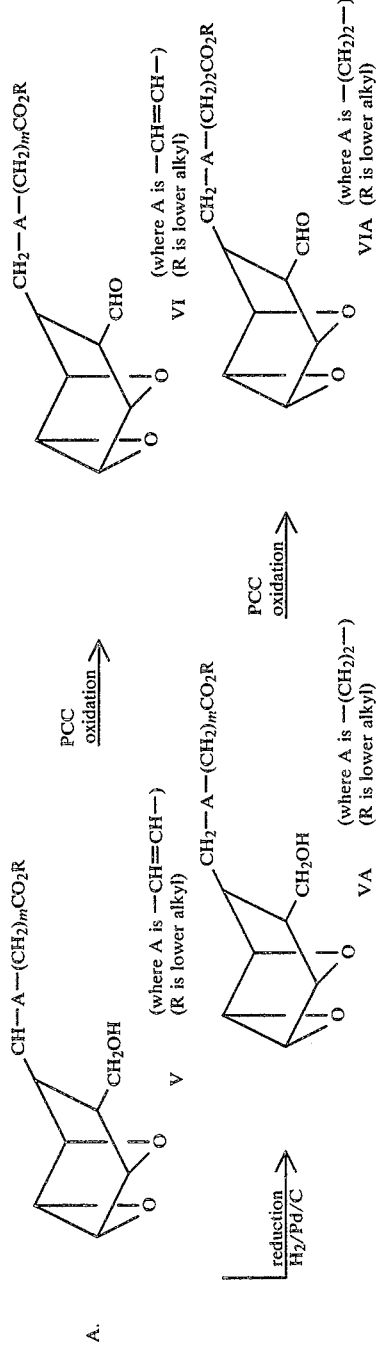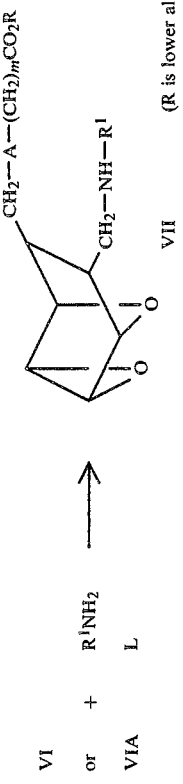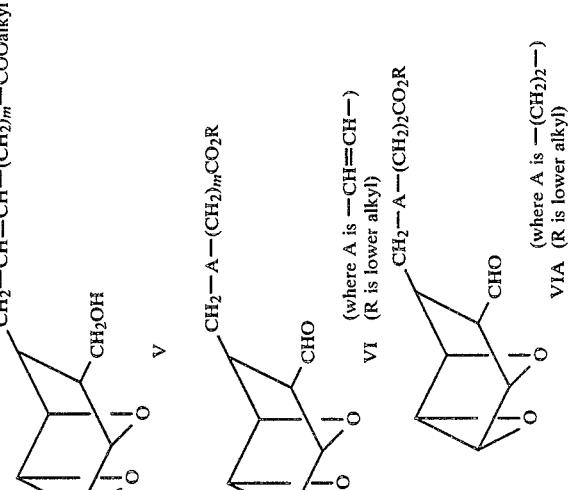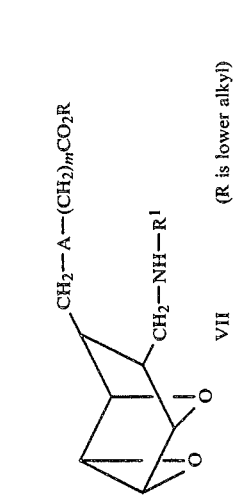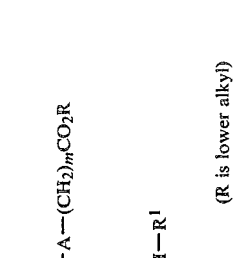
A.
B. Where n is 1 and R¹ is lower alkyl, cycloalkyl, cycloalkylalkyl or lower alkenyl
C. Where n is 1 and R¹ is $-O(CH_2)_pR^3$ where R is alkyl or aralkyl and p is 1 to 5, that is, lower alkoxy or aralkoxy

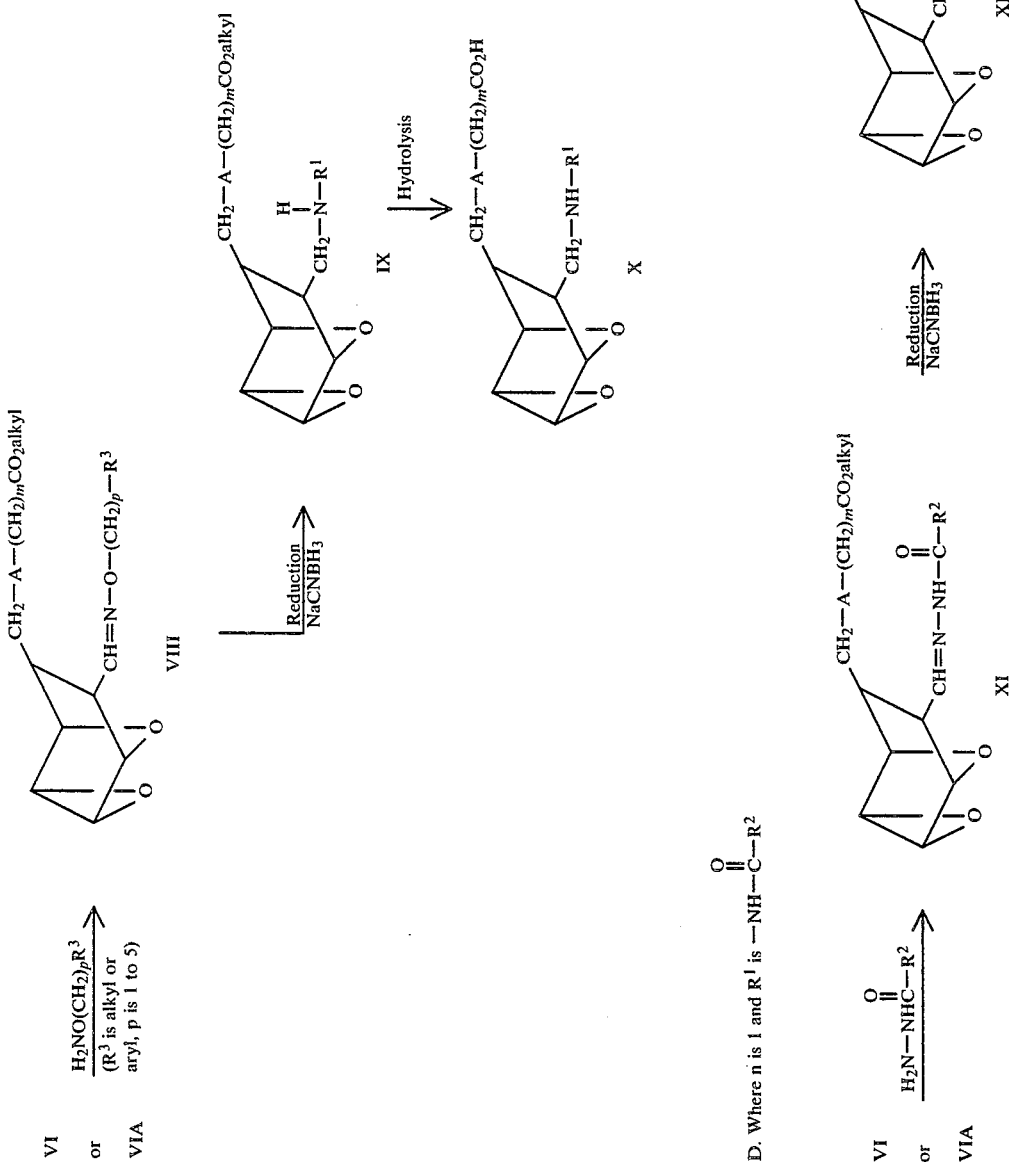

-continued

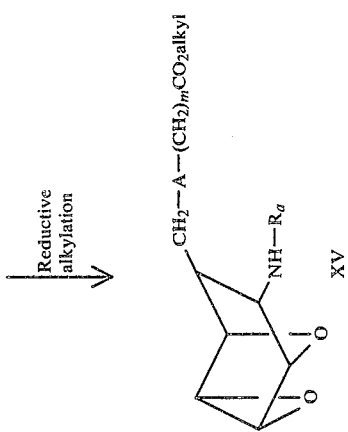

XI (where A is —(CH$_2$)$_2$— or —CH=CH—)

$\xrightarrow{\text{Hydrogenation} \atop \text{H}_2/\text{Pd—C}}$

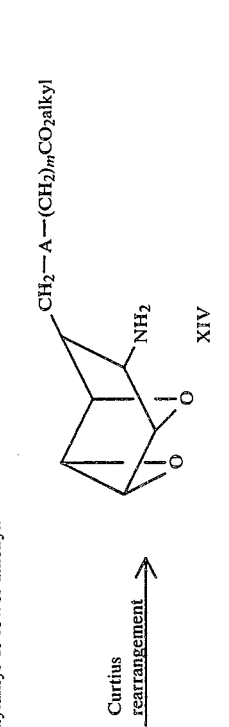

XII (where A is (CH$_2$)$_2$)

E. Where n is 0 and R$^1$ is —NH—R$_a$ wherein R$_a$ is lower alkyl, cycloalkyl, cycloalkylalkyl or lower alkenyl.

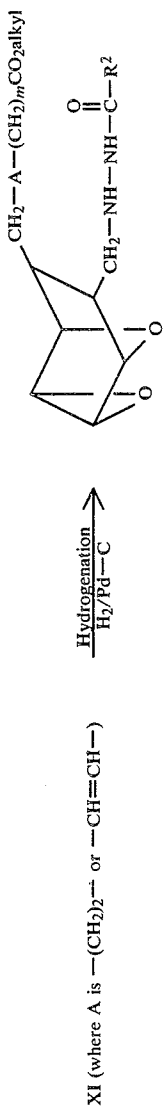

V or VA $\xrightarrow{\text{Oxidation}}$

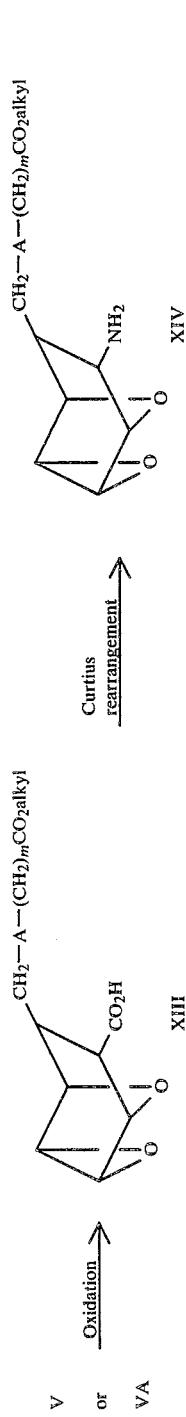

XIII $\xrightarrow{\text{Curtius} \atop \text{rearrangement}}$

XIV $\xrightarrow{\text{Reductive} \atop \text{alkylation}}$

XV

F. Where n is 2 to 5

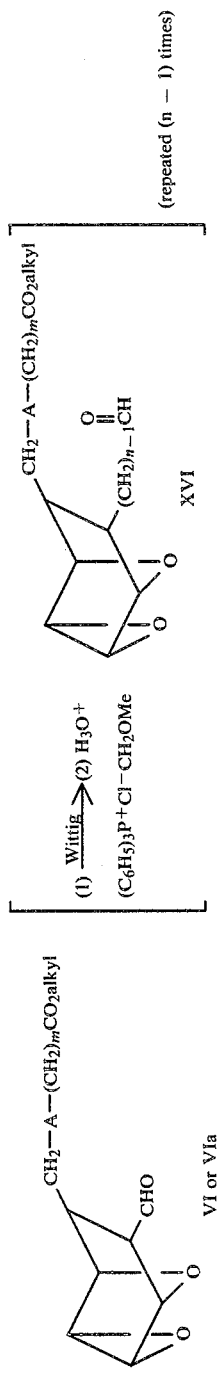

VI or VIa $\left[ \xrightarrow[\text{(C}_6\text{H}_5)_3\text{P}^+\text{Cl}^-\text{CH}_2\text{OMe}]{\text{(1) Wittig} \atop \text{(2) H}_3\text{O}^+} \right.$

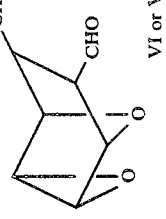

XVI $\left. \right]$ (repeated (n − 1) times)

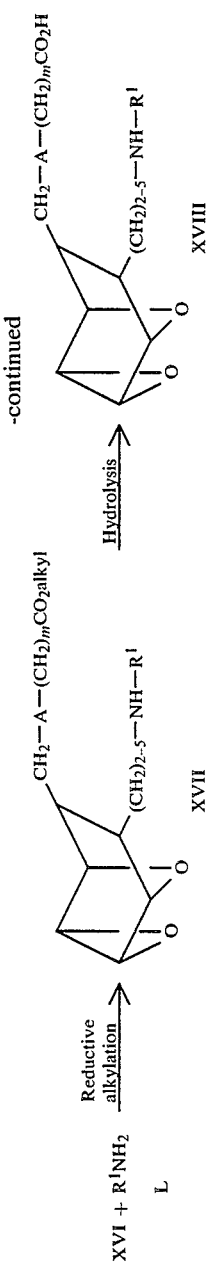

As seen from the reaction sequence set out above, compounds of the invention may be formed by treating II with diisobutyl aluminum hydride (DIBALH) in the presence of an inert solvent such as toluene or tetrahydrofuran at reduced temperatures of from about −70° to about −85° C. to form epoxy aldehyde III (which itself is a new compound)

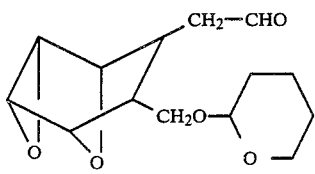   III

Epoxy aldehyde III in appropriate solvent such as tetrahydrofuran is then reacted with a suspension formed by mixing dry carboxyalkyltriphenylphosphonium halide K

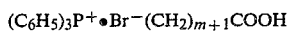   K in tetrahydrofuran with potassium t-amylate in toluene at reduced temperature and the reaction product treated with ethereal diazoalkane to form the ester IV (which also is a novel compound)

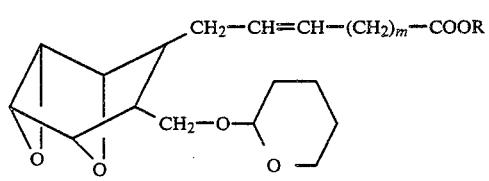   IV (wherein R is lower alkyl).

Compound IV is dissolved in methanol and is then hydrolyzed by treatment with strong acid such as HCl, Amberlyst resin or acetic acid to form alcohol V (which also is a novel compound)

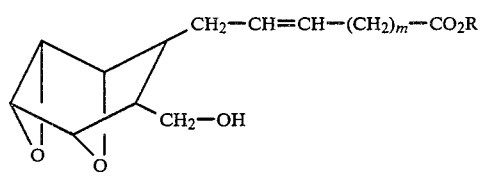   V (wherein R is lower alkyl) which also is a novel compound.

As seen in reaction sequence "A", the epoxy ester V (wherein A is CH=CH) containing the hydroxymethyl group is used to form epoxy aldehyde VI by subjecting epoxy ester V to PCC oxidation, for example, by reacting V with pyridiniumchlorochromate in methylene chloride

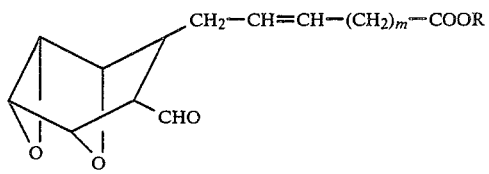   VI wherein R is lower alkyl (which also is a novel compound).

To form the aldehyde VIA (where A is $(CH_2)_2$), compound V is reduced, for example with hydrogen over a palladium on carbon catalyst, to form hydroxymethyl compound VIA (where A is $(C_2)_2$) and compound VA is subjected to a PCC oxidation to form aldehyde VIA (where A is $(CH_2)_2$).

As seen in reaction sequence "B", compounds of the invention where n is 1 and $R^1$ is lower alkyl, cycloalkyl, cycloalkylalkyl or lower alkenyl, that is,

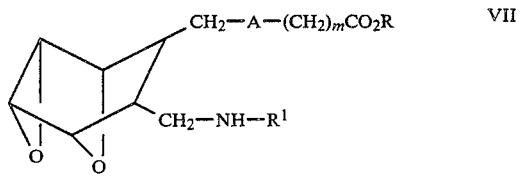   VII are prepared by reacting aldehyde VI or VIA with an alkylamine L ($R^1NH_2$)   L employing a molar ratio of VI or VIA:alkylamine of within the range of from about 0.8:1 to about 1:1, in a solvent such as methanol or ethanol and a reducing agent such as sodium borohydride or sodium cyanoborohydride.

As seen in reaction sequence "C", compounds of the invention wherein n is 1 and $R^1$ is lower alkoxy or aralkoxy, that is

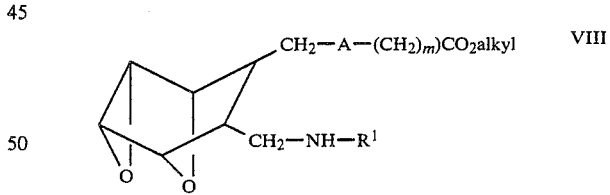   VIII are prepared by reacting aldehyde VI or VIA with an alkoxyamine, such as of the structure

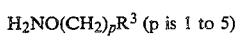   M employing a molar ratio of VI or VIA:M of within the range of from about 0.8:1 to about 1:1 in a solvent such as methanol or ethanol.

Compound VIII is then reduced, such as by reacting VIII with a reducing agent such as $NaBH_4$ or $NaCNBH_3$ in a solvent such as methanol or ethanol and in the presence of acetic acid to form the compound of structure IX.

Where p is 0 so that $R_1$ is aryloxy, then compound V or VA is first hydrolyzed by reacting same with lithium hydroxide or sodium hydroxide to form the corresponding carboxylic acid VB

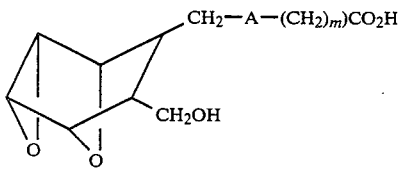 VB (where A is —(CH$_2$)$_2$— or —CH=CH—)
which is then subjected to a PCC or Collins oxidation (as described above) to form the corresponding aldehyde VIB

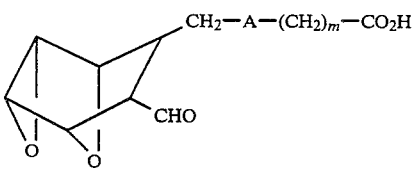 VIB

Aldehyde VIB is reacted with an aryloxyamine N

 N (where p is O and R$^3$ is aryl) to form compound VIIIA

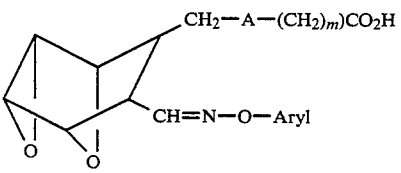 VIIIA

Compound VIIIA is then reduced with NaCNBH$_3$ in the presence of acetic acid to form the aryloxyamine of the invention

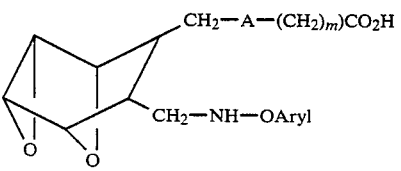 XA

In the reaction sequence identified as "D", compound of the invention wherein n is 1 and R$^1$ is

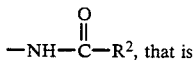, that is

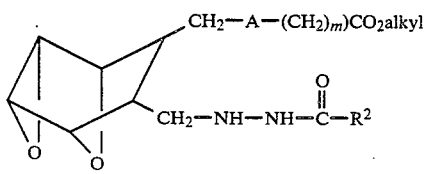 IX are prepared by reacting aldehyde VI or VIA with a hydrazine derivative

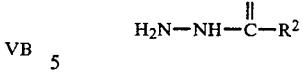

to form compound XI, employing a molar ratio of VI or VIA:O of within the range of from about 0.8:1 to about 1:1, in a protic solvent such as methanol or ethanol.

Compound XI is then reduced, such as by reacting XI with a reducing agent, such as NaBH$_3$CN or NaBH$_4$ in the presence of acetic acid or hydrogen with palladium on carbon as a catalyst to form compound XII.

Compound XII where A is —(CH$_2$)$_2$—or —CH=CH— may also be prepared by subjecting compound XI (where A is —(CH$_2$)$_2$— or —CH=CH—) to hydrogenation by reacting XI with hydrogen gas over a palladium on carbon catalyst.

In the reaction sequence identified as "E", compounds of the invention wherein n is 0 and R$^1$ is —N—H—R$_a$, wherein R$_a$ is lower alkyl, cycloalkyl, cycloalkylalkyl or lower alkenyl

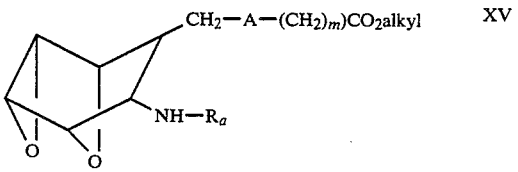 XV are prepared by oxidizing hydroxymethyl compound V of VA, such as by reacting V or VA with an oxidizing agent, such as pyridinium dichromate in a solvent, such as dimethylformamide, to form the acid XIII. Acid XIII is subjected to a Curtius rearrangement reaction which involves reacting acid XIII with carbonyldiimidazole in the presence of an inert organic solvent, such as toluene, under an inert atmosphere, followed by addition of trimethylsilylazide to the reaction mixture and the resulting isocyanate solution is converted to the amine XIV by reacting same with hydrochloric acid.

The amine XIV is subjected to reductive alkylation by reacting same with heptanal in a solvent, such as methanol and then adding sodium borohydride or other reducing agent, such as sodium cyanoborohydride in the presence of acetic acid to form the compound XV.

The reaction sequence identified as "F" is employed to prepare the compounds of the invention where n is 2 to 5, that is,

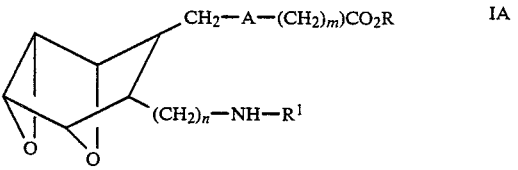 IA (where n is 2 to 5)
The aldehyde VI or VIA is used to prepare aldehyde XVI (where n is 2-5) by carrying out a homologation sequence, such as a Wittig reaction with (C$_6$H$_5$)$_3$P=CHOMe followed by hydrolysis, (n−1) times. The aldehyde XVI (where n=2-5) is thus carried on to the compounds of this invention where n is 2-5, that is

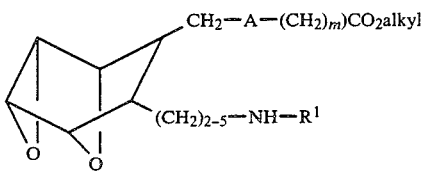

by reductive amination employing an amine of structure L in a weight ratio of XVI:L of within the range of from about 0.8:1 to about 1:1 and a reducing agent such as sodium borohydride or sodium cyanoborohydride in a solvent such as methanol or ethanol and in the presence of acetic acid to form the compound of structure XVII.

The esters VII, VIII, XII, XV and XVII can be converted to the free acid, that is, to

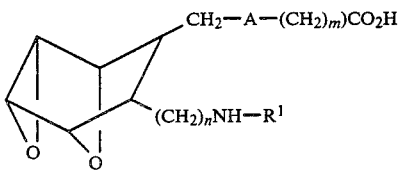

X (A is —CH=CH—)
XA (A is (CH$_2$)$_2$)

by treating the esters with a base, such as lithium hydroxide, followed by neutralization with an acid, such as dilute hydrochloric acid or oxalic acid.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared as shown in the working Examples which follow and by employing starting materials and following the procedures as outlined in U.S. Pat. No. 4,143,054. Examples of such stereoisomers are set out below.

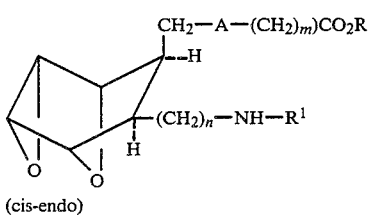
(cis-endo)

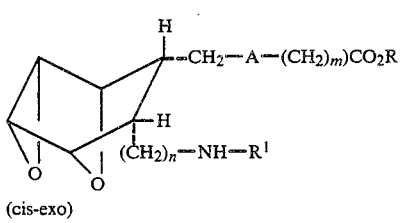
(cis-exo)

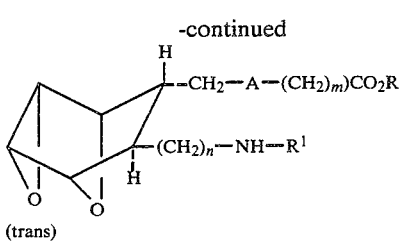
(trans)

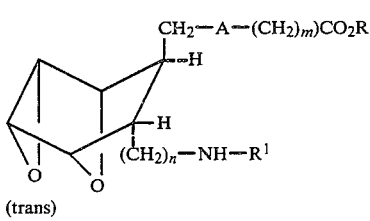
(trans)

The nucleus in each of the compounds of the invention is depicted as

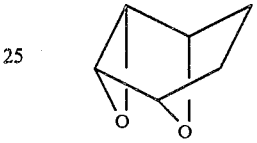

for matter of convenience; it will also be appreciated that the nucleus in the compounds of the invention may be depicted as

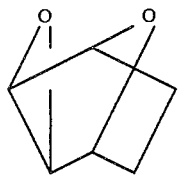

The compounds of this invention are cardiovascular agents useful as platelet aggregation inhibitors, such as inhibiting arachidonic acid-induced platelet aggregation (e.g., for treatment of thrombotic disease, such as coronary or cerebral thromboses) and in inhibiting bronchoconstriction as induced by asthma. They are also selective thromboxane A$_2$ receptor antagonists and synthetase inhibitors, e.g., having a vasodilatory effect for treatment of myocardial ischemic disease, such as angina pectoris.

The compounds of this invention may be used in combination with a cyclic AMP phosphodiesterase (PDE) inhibitor such as theophylline or papaverine in the preparation and storage of platelet concentrates.

The compounds of the invention can be administered orally or parenterally to various mammalian species known to be subject to such maladies, e.g., humans, cats, dogs, and the like in an effective amount within the dosage range of about 1 to 100 mg/kg, preferably about 1 to 50 mg/kg and especially about 2 to 25 mg/kg on a regimen in single or 2 to 4 divided daily doses.

The compounds of the invention may also be administered topically to any of the above mammalian species in amounts of from about 0.1 to 10 mg/kg in single or 2 to 4 divided daily doses.

The active substance can be utilized in a composition such as tablet, capsule, solution or suspension containing about 5 to about 500 mg per unit of dosage of a compound or mixture of compounds of formula I. They may be compounded in conventional matter with a physiologically acceptable vehicle or carrier, excipient, binder, preservative, stabilizer, flavor, etc. as called for by accepted pharmaceutical practice. Also as indicated in the discussion above, certain members additionally serve as intermediates for other members of the group.

The following Examples represent preferred embodiments of the invention. Unless otherwise indicated, all temperatures are expressed in degrees Centigrade.

EXAMPLE 1

[1α,2β(5Z),3β,4α,5α,6α]-7-[5,6-Epoxy-3-[[2-[(phenylamino)carbonyl]hydrazino]methyl]-7-oxabicyclo[2.2.1]hept-2-yl]-5-heptenoic acid, methyl ester

A. 7-Oxabicyclo[2.2.1]-5-heptene-2,3-dimethanol

To a suspension of 6.84 g of lithium aluminum hydride (180 mmol) in 200 ml of freshly distilled THF, cooled in an ice-water bath was added dropwise, a solution of 20 g of 7-oxabicyclo[2.2.1]-5-heptene-2,3-dicarboxylic anhydride (120 mmol) in 150 ml of dry THF, over a period of 1 hour. After the addition, the cooling bath was removed and the reaction mixture was stirred at room temperature for 24 hours. The reaction mixture was now cooled in an ice-water bath and excess of hydride was destroyed by slow addition of freshly prepared saturated sodium sulfate solution. Addition was continued until all the inorganic salts were precipitated as white granular solids. Anhydrous magnesium sulfate was added to the reaction mixture and it was filtered. The residue was thoroughly washed with methylene chloride. The residue was taken up in 500 ml of 10% acetonitrile in ethyl acetate, stirred for 30 minutes and finally was filtered. The combined filtrate was concentrated under reduced pressure. The crude residue was chromatographed on a silica gel column. Elution with 50% ethyl acetate in hexane, followed by ethyl acetate and finally with 10% methanol in ethyl acetate afforded 17.25 g of title diol as a colorless viscous oil.

B. 7-Oxabicyclo[2.2.1]-5-heptene-2,3-dimethanol carbonate

To a solution of 16.73 g of Part A diol (107.4 mmole) in 200 ml of freshly distilled THF, cooled in an ice-water bath was added dropwise 90 ml of a 12.5% by weight solution of phosgene in toluene (112.5 mmol), over a period of 45 minutes. The reaction mixture was stirred for an additional 15 minutes, whereupon argon was bubbled through to remove excess of phosgene and hydrogen chloride formed during the reaction. The reaction mixture was now concentrated under reduced pressure. The crude monochloroformate was now dissolved in 250 ml of methylene chloride and cooled at −50° C. in a dry ice-acetone bath. A solution of 25 ml of pyridine in 50 ml of methylene chloride was now added dropwise over a period of 20 minutes. An immediate white precipitate was formed upon addition. The reation mixture was left at −50° C. for an additional 30 minutes, whereupon the cooling bath was removed and the reaction mixture was washed thoroughly with water. The methylene chloride layer was dried over anhydrous magnesium sulfate, filtered and the filtrate was concentrated under reduced pressure. The crude residue was triturated with ether, cooled at 0° C. and the precipitated title carbonate was filtered off. 15.25 g of white crystalline title carbonate was obtained.

C. 2-Hydroxymethyl-3-isopropyloxycarbonyloxymethyl-7-oxabicyclo[2.2.1]heptene To a suspension of 15.25 g of Part B cyclic carbonate (83.8 mmole) in 200 ml of isopropyl alcohol was added with stirring 1 g of p-toluene sulfonic acid. The reaction mixture was heated under reflux for 8 hours whereupon it was cooled and isopropanol was removed by distillation under reduced pressure. The crude residue was dissolved in methylene chloride and washed with aqueous sodium bicarbonate solution. The aqueous layer was extracted several times with methylene chloride. The combined methylene chloride extract was dried over anhydrous magnesium sulfate and was then concentrated under reduced pressure to obtain 22.53 g of title isopropyloxycarbonate as a viscous oil.

D. 2-p-Toluenesulfonyloxymethyl-3-isopropyloxycarbonyloxymethyl-7-oxabicyclo[2.2.1]heptene To a solution of 22.53 g of Part C isopropyloxycarbonate (84 mmole) in 100 ml of pyridine was added with stirring 19.2 g of p-toluene sulfonyl chloride (101 mmole) at 0°–5° C. The reaction mixture was stirred at room temperature for 24 hours, whereupon it was diluted with methylene chloride and washed thoroughly with water, saturated copper sulfate solution and finally with water. The combined aqueous layer was extracted with two 200 ml portions of methylene chloride. The combined methylene chloride extract was dried over anhydrous magnesium sulfate and finally was concentrated under reduced pressure. The crude residue was triturated with ether, cooled at 0° C. and the precipitate title tosylate (28.3 g) was filtered off. The mother liquor was concentrated and chromatographed on a silica gel column to obtain additional 5.2 g of crystalline title tosylate (eluting solvent 15–30% ethyl acetate in hexane).

E. 2-Cyanomethyl-3-isopropyloxycarbonyloxymethyl-7-oxabicyclo[2.2.1]heptene

To a solution of 5.3 g of Part D tosylate (12.99 mmole) in 50 ml of dry dimethylsulfoxide was added with stirring 1.28 g of powdered sodium cyanide (26 mmole). The reaction mixture was placed on an oil bath (bath temperature 90°–95° C.) and heated for 2 hours. It was now cooled and diluted with 200 ml of ether. The reaction mixture was now thoroughly washed with water. The combined aqueous extract was extracted with two 150 ml of ether. The ether layer was now dried over anhydrous magnesium sulfate and concentrated under reduced pressure. The crude residue was chromatographed on a silica gel column. Elution with 25–50% ehtyl acetate in hexane afforded 2.58 g of title cyano-carbonate.

F. 2-Cyanomethyl-3-hyroxymethyl-7-oxabicyclo[2.2.1]heptene

To a solution of 1 g of potassium carbonate in 25 ml of water and 75 ml of methanol, cooled in an ice-water bath was added with stirring a solution of 2.58 g of Part E cyano-carbonate (9.8 mmol) in 10 ml of methanol. After 15 minutes, the cooling bath was removed and the reaction mixture was allowed to stand at room temperature for additional 6 hours, whereupon it was acidified with 1N aqueous hydrochloric acid solution. Most of methanol was now removed by distillation under reduced pressure. The residue was now exhaustively extracted with methylene chloride (X12) (after saturating it with sodium chloride). The combined organic extract was dried over anhydrous magnesium sulfate and concentrated under reduced pressure. The crude residue was chromatographed on a silica gel column and eluted with 25-50% ethyl acetate in hexane, followed by ethyl acetate to obtain 1.23 g of title cyano alcohol.

G.
2-Cyanomethyl-3-tetrahydropyranyloxymethyl-7-oxabicyclo[2.2.1]heptene A solution of 1.23 g of Part F cyano-alcohol (7.36 mmole) in 20 ml of dry methylene chloride was treated with 800 ml of dihydropyran (8.89 mmole) and catalytic amount of p-toluene sulfonic acid at 0°-5° C. After 4 hours, the reaction mixture was diluted with ether and washed with aqueous sodium bicarbonate solution. The aqueous layer was reextracted twice with ether. The combined organic extract was dried over anhydrous magnesium sulfate and concentrated under reduced pressure. The crude residue was chromatographed on a silica gel column and eluted with 20-25% ethyl acetate in hexane to obtain 1.61 g of title tetrahydropyranyl ether.

H.
5,6-Epoxy-2-cyanomethyl-3-tetrahydropyranyloxymethyl-7-oxabicyclo[2.2.1]heptene A solution of 1.61 g of Part G cyano ether (6.4 mmole) in 20 ml of dry methylene chloride was treated with 1.66 g of 80% pure m-chloroperoxybenzoic acid (9.6 mmole) at 0°-5° C. After a few minutes, the cooling-bath was removed and the reaction mixture was let stand at room temperature for 6 hours. The reaction mixture was now diluted with ether and excess of peracid was decomposed by addition of aqueous sodium meta-bisulfite solution. After stirring for 30 minutes, the organic layer was separated and the aqueous layer was extracted twice with methylene chloride. The combined organic extract was dried over anhydrous magnesium sulfate and concentrated under reduced pressure. Purification by chromatography on a silica gel column (eluting solvent 25-67% ethyl acetate in hexane) afforded 1.57 g of title epoxide.

J.
5,6-Epoxy-2-formylmethyl-3-tetrahydropyranyloxymethyl-7-oxabicyclo[2.2.1]heptane To a solution of Part H epoxy-nitrile (1.57 g, 5.88 mmole) in 25 ml of toluene, cooled at −78° C. in a dry ice-acetone bath was added with stirring, 6.8 ml of a 25% by weight solution of diisobutylaluminum hydride in toluene (∼12 mmole), dropwise over a period of 5 minutes. After 4 hours at −78° C., excess of hydride was destroyed by dropwise addition of 1 ml of glacial acetic acid. The cooling bath was removed and 20 g of silica gel was added to the reaction mixture with stirring, followed by 1.5 ml of water dropwise. Stirring was continued for 30 minutes, whereupon the reaction mixture was filtered and the residual silica gel was washed successively with THF, 5% acetonitrile in ethyl acetate and finally with acetone. The combined filtrate was concentrated under reduced pressure and the crude residue was chromatographed on a silica gel column. Elution with 50% ethyl acetate in hexane, followed by ethyl acetate afforded 1.16 g of title epoxyaldehyde which crystallized on standing at −20° C.

K.
[1α,2β(5Z),3β,4α,5α,6α]-7-[5,6-Epoxy-3-(tetrahydropyranyloxymethyl)-7-oxabicyclo[2.2.1]hept-2-yl]-5-heptenoic acid, methyl ester A suspension of 5.77 g of freshly dried carboxybutyltriphenylphosphonium bromide (13.03 mmol), in 50 ml of freshly distilled THF, cooled in an ice-water bath was treated dropwise with 12 ml of a 1.5M solution of K-t-amylate in toluene (19.2 mmole). The yellow-orange suspension was stirred at 0° C. for 30 minutes and finally at room temperature for 1 hour, whereupon it was cooled to −20° C. and a solution of 2.33 g of Part J epoxy aldehyde (8.69 mmole) in 10 ml of dry THF was added dropwise over a period of several minutes. An instant discolorization of the ylide solution was observed. The reaction mixture was stirred at −20° C. for 2 hours, whereupon it was warmed to 0° C. and left for 15 minutes, prior to addition of glacial acetic acid. The reaction mixture was now diluted with ether and washed with water. The ether extract was washed several times with saturated sodium bicarbonate solution. The combined aqueous extract was now washed with ether (X2). The aqueous layer was now carefully acidified with 1N aqueous hydrochloric acid to pH 2. It was now extracted with ether and then with methylene chloride. The combined ether and methylene chloride extract was dried over anhydrous magnesium sulfate and concentrated under reduced pressure. The crude residue was diluted with 75 ml of ether, cooled in an ice-water bath and an etheral diazomethane solution was added dropwise until the color persisted. After 30 minutes, excess diazomethane was removed by bubbling argon through the reaction mixture. It was now concentrated and the crude residue was chromatographed on a silica gel column. Elution with 15-40% ethyl acetate in hexane afforded 1.27 g of title 5Z-ester (contaminated with 10-15% of undesired 5E ester).

L.
[1α,2β(5Z),3β,4α,5α,6α]-7-[5,6-Epoxy-3-hydroxymethyl-7-oxabicyclo[2.2.1]hept-2-yl]-5-heptenoic acid, methyl ester To a solution of 1.27 g of Part K tetrahydropyranyl ether (3.46 mmole) in 30 ml of methanol was added with stirring 250 mg of powdered and dried Amberlyst-15. After 6 hours at room temperature, the reaction mixture was diluted with ether and anhydrous magnesium sulfate was added. It was now filtered and the residual solid was washed thoroughly with ether. The combined organic extract was dried over anhydrous magnesium sulfate and concentrated under reduced pressure. The crude residue was chromatographed on a silica gel column and eluted with 50-75% ethyl acetate in hexane to obtain 892 mg of title alcohol ester.

M.
[1α,2β(5Z),3β,4α,5α,6α]-7-[5,6-Epoxy-3-formyl-7-oxabicyclo[2.2.1]hept-2-yl]-5-heptenoic acid, methyl ester To a suspension of 325 mg of pyridinium chlorochromate and 325 mg of celite in 20 ml of dry methylene chloride was added with stirring a solution of 211 mg Part L alcohol ester (0.75 mmole) in 2 ml of methylene chloride. After 4 hours at room temperature, the reaction mixture was diluted with 100 ml of ether and filtered through a pad of florisil. Florisil was washed several times with ether and ethyl acetate. The combined organic extract was washed with water, dried over anhydrous magnesium sulfate and was then concentrated under reduced pressure to obtain 174 mg of title aldehyde.

N.

[1α,2β(5Z),3β,4α,5α,6α]-7-[5,6-Epoxy-3-[[2-[(phenylamino)carbonyl]hydrazino]methyl]-7-oxabicyclo[2.2.1]hept-2-yl]-5-heptenoic acid, methyl ester To a solution of 85 mg of Part M aldehyde (0.30 mmole) in 3 ml of ethanol at 25° C. was added 90 mg of 4-phenylsemicarbazide (0.60 mmole, 2 equiv). After stirring at 25° C. for 20 hours, the mixture was concentrated. The residue was purified on a silica gel column, with 62.5% EtOAc/hexanes as eluting solvents, to give 100 mg of title ester as a white foam.

O.

[1α,2β(5Z),3β,4α,5α,6α]-7-[5,6-Epoxy-3-[[2-[(phenylamino)carbonyl]hydrazino]methyl]-7-oxabicyclo[2.2.1]hept-2-yl]-5-heptenoic acid, methyl ester To a solution of 100 mg of Example 1 ester (0.24 mmole) and 31 mg of sodium cyanoborohydride (0.5 mmole, 2 equiv.) at 25° C. was added dropwise 0.9 ml of glacial acetic acid. After stirring at 25° C. for 20 hours, 30 ml of EtOAc and 15 ml of a saturated NaHCO$_3$ solution were added. The layers were separated and the aqueous layer was extracted with two 15 ml portions of EtOAc. The combined organic layer was washed with two 10 ml portions of 1N sodium hydroxide solution and three 10 ml portions of brine. The organic layer was dried over anhydrous MgS$_4$ and concentrated to give 98 mg of a crude solid. Recrystallization with EtOAc/ether gave 76 mg of title ester as a white solid.

TLC: silica gel; EtOAc; R$_f$~0.2.

Anal Calcd for C$_{22}$H$_{29}$N$_3$O$_5$; 0.3 H$_2$O: C, 62.78; H, 7.09; N, 9.98.

Found: C, 62.81; H, 7.02; N, 9.94.

EXAMPLE 1A

[1α,2β(5Z),3β,4α,5α,6α]-7-[5,6-Epoxy-3-[[2-[(Phenylamino)carbonyl]hydrazino]methyl]-7-oxabicyclo[2.2.1]hept-2-yl]-5-heptenoic acid To a solution of 76 mg of Example 1 title O ester in 1 ml of THF is added with stirring 500 ml of a 1N aqueous lithium hydroxide solution. After stirring at room temperature for several hours, the reaction mixture is acidified with aqueous oxalic acid solution and extracted with methylene chloride. The methylene chloride extract is dried over anhydrous magnesium sulfate and concentrated. The crude residue is chromatographed on a silica gel column and eluted with 5–10% methanol in methylene chloride to obtain the title acid.

EXAMPLE 2

[1α,2β(5Z),3β,4α,5α,6α]-7-[5,6-Epoxy-3-[(Hexylamino)methyl]-7-oxabicyclo[2.2.1]hept-2-yl]-5-heptenoic acid

A.

[1α,2β(5Z),3β,4α,5α,6α]-7-[5,6-Epoxy-3-[(Hexylamino)methyl]-7-oxabicyclo[2.2.1]hept-2-yl]-5-heptenoic acid, methyl ester To 140 mg (0.50 mmole, 1 eq) of the Example 1 Part M aldehyde in 3 ml of anhydrous methanol under an argon atmosphere at 25° is added 101.1 mg (1.0 mmole, 2 eq) of hexylamine and ca. 300 mg of activated crushed 3 Å molecular sieves. The reaction was stirred for 96 hours, diluted with 2 ml of anhydrous methanol, cooled to 0° and an excess of sodium borohydride is added. This reaction mixture is stirred for 30 minutes, quenched with 1 ml of acetone, diluted with 100 ml of ether and washed successively with 50 ml of water and 50 ml of brine, and dried over anhydrous magnesium sulfate. The product is purified by flash chromatography on LP-1 silica using a 167/15/1 chloroform:methanol:formic acid solution as the eluant to provide the title compound as an oil.

[1α,2β(5Z),3β,4α,5α,6α]-7-[5,6-Epoxy-3-[(Hexylamino)methyl]-7-oxabicyclo[2.2.1]hept-2-yl]]-5-heptenoic acid 257 mg (0.43 mmol) of the title A ester in 10 ml of a 1N sodium hydroxide solution is refluxed for 45 minutes, cooled, neutralized to ca. pH 6.5 with dilute hydrochloric acid, and extracted with two 85 ml portions of ethyl acetate to provide an oil. This material is recrystallized twice from acetonitrile to provide the title product.

EXAMPLE 3

(1α,2β,3β,4α,5α,6α)-7-[5,6-Epoxy-3-[(hexylamino)methyl]-7-oxabicyclo[2.2.1]hept-2-yl]heptanoic acid

A.

(1α,2β,3β,4α,5α,6α)-[5,6-Epoxy-3-(hydroxymethyl)-7-oxabicyclo[2.2.1]hept-2-yl]heptanoic acid, methyl ester To 846 mg (3.0 mmole) of the hydroxymethyl epoxy compound as prepared in Example 1 Part L dissolved in 120 ml of ethyl acetate is added, under an argon atmosphere, 160 mg of 5% Pd on carbon. The argon atmosphere is exchanged for a slight positive pressure of hydrogen and the reaction is stirred for 8 hours at 25°, filtered through a celite plug and evaporated to provide the title A compound.

B.

(1α,2β,3β,4α,5α,6α)-7-[5,6-Epoxy-3-formyl-7-oxabicyclo[2.2.1]hept-2-yl]heptanoic acid, methyl ester To 1.21 g (5.6 mmole, 2.0 equiv) of pyridinium chlorochromate (PCC) and 20 ml of anhydrous CH$_2$Cl$_2$ is added, under an argon atmosphere, 795 mg (2.8 mmole) of the title A alcohol in 2 ml of CH$_2$Cl$_2$. The reaction is stirred for 2 hours at 25°, diluted with 100 ml of ether, filtered through a pad of florisil, and evaporated to furnish the title B compound.

C.
(1α,2β,3β,4α,5α,6α)-7-[5,6-Epoxy-3-[(hexylamino)methyl]-7-oxabicyclo[2.2.1]hept-2-yl]heptanoic acid Following the procedure of Example 2 except substituting the Part C aldehyde for the Example 1 Part M aldehyde, the title product is obtained.

EXAMPLE 4

[1α,2β(5Z),3β,4α,5α,6α]-7-[5,6-Epoxy-3-[[(phenylmethoxy)amino]methyl]-7-oxabicyclo[2.2.1]hept-2-yl]]-5-heptenoic acid

A.
[1α,2β(5Z),3β,4α,5α,6α]-7-[5,6-Epoxy-3-[[(phenylmethoxy)imino]methyl]-7-oxabicyclo[2.2.1]hept-2-yl]-5-heptenoic acid, methyl ester NaOAc (164 mg, 2 mmol) is added to a magnetically stirred suspension of O-benzylhydroxylamine hydrochloride (320 mg, 2 mmol) in EtOH (8 ml) at room temperature. Then, [1α,262 (5Z),3β,4α,5α,6α]-7-[5,6-epoxy-3-formyl-7-oxabicyclo[2.2.1]hept-2-yl]-5-heptenoic acid, methyl ester prepared as described in Example 1, Part M (560 mg, 2 mmol) in EtOH (2 ml) is added and stirred for 1 hour at room temperature. The reaction is poured into Et₂O (100 ml), which is washed with 1N HCl (20 ml×2), saturated NaHCO₃ (20 ml×2), brine (20 ml×2), and dried over MgSO₄. Filtration and evaporation of solvents gives the title compound which is purified by a silica gel column (silica 60, 30 g) eluted with Et₂O/petroleum ether (2/3).

B. [1α,2β(5Z),3β, 4α,5α,6α]-7-[5,6-Epoxy-3-[[(Phenylmethoxy)amino]-methyl]-7-oxabicyclo[2.2.1]hept-2-yl]-5-heptenoic acid, methyl ester NaBH₃CN (57 mg, 0.92 mmol) is added to a magnetically stirred solution of oxime prepared as described in Part A (272 mg, 0.71 mmol) in MeOH (8.5 ml), followed by addition of AcOH (1.5 ml) dropwise. After 2¼ hours stirring at room temperature, additional NaBH₃CN (40 mg, 0.64 mmol) and AcOH (1 ml) are added. Stirring is continued at room temperature for 1 hour. Then, the reaction is quenched by addition of 2N HCl to pH 1 and stirred for 30 minutes. The reaction is basified by addition of saturated NaHCO₃. The products are extracted with Et₂O (100 ml×2). The combined ether layers are washed with brine and dried over MgSO₄. Filtration and evaporation of solvent gives the title compound in the form of an oil which is purified by a silica gel column and eluted with ether/petroleum ether (1/1) to give title compound.

EXAMPLE 5

[1α,2β(5Z),3β,4α,5α,6α]-7-[5,6-Epoxy-3-[[(Phenylmethoxy)amino]methyl]-7-oxabicyclo[2.2.1]hept-2-yl]-5-heptenoic acid 1N LiOH (6 ml) is added to the Example 4 ester (227 mg, 0.59 mmol) in THF (30 ml) and H₂O 6 ml) at room temperature. After 6 hours stirring at room temperature, the reaction is quenched by addition of 1N HCl (6 ml) and poured into brine (20 ml). The products are extracted with ether (100 ml×3). The combined ether layers are washed with brine (50 ml×3) and dried over Na₂SO₄. Filtration and evaporation of solvent yields an oil which is purified by a silica gel column (silica 60, 20 g) eluted with CH₂Cl₂/MeOH (9.4/0.6) to give the title product.

EXAMPLE 6

(1α,2β,3β,4α,5α,6α)-7-5,6-Epoxy-3-[(Phenylmethoxy)amino]methyl]-7-oxabicyclo[2.2.1]hept-2-yl]heptanoic acid Following the procedure of Example 3 and Examples 4 and 5 except substituting O-benzylhydroxylamine hydrochloride for hexylamine, the title compound is obtained.

EXAMPLE 7

[1α,2β(5Z),3β,4α,5α,6α]-7-[5,6-Epoxy-3-(Heptylamino)-7-oxabicyclo[2.2.1]hept-2-yl]-5-heptenoic acid

A.
[1α,2β(5Z),3β,4α,5α,6α]-7-[5,6-Epoxy-3-carboxy-7-oxabicyclo[2.2.1]hept-2-yl]-5-heptenoic acid, methyl ester To 5.3 g (19.9 mmole) of hydroxymethyl compound prepared as described in Example 1 Part L in 300 ml of dimethylformamide is added 26.2 g (69.7 mmole, 3.5 eq) of pyridinium dichromate. The reaction is stirred for 24 hours, diluted with 300 ml of water and extracted with three 200 ml portions of ether. The ethereal layer is washed with three 100 ml portions of water and dried over anhydrous magnesium sulfate. The crude product is purified by flash chromatography using LP-1 silica and a gradient of 20% ether in pentane to 40% ether in pentane to provide the title acid.

B.
[1α,2β(5Z),3β,4α,5α,6α]-7-[5,6-Epoxy-3-Amino-7-oxabicyclo[2.2.1]hept-2-yl]-5-heptenoic acid, methyl ester To 306 mg (1.04 mmole) of the title A acid in 3 ml of anhydrous toluene is added 169 mg (1.04 mmole, 1 eq) of carbonyldiimidazole at 25° under an argon atmosphere. The reaction is stirred for 1 hour and 230.4 mg (2.08 mmole, 2 eq) of trimethylsilylazide is added. The reaction mixture is stirred for an additional 3 hours, diluted with 25 ml of toluene and washed successfully with 10 ml of cold 5% potassium bisulfate, and 10 ml of brine and dried over anhydrous magnesium sulfate. This organic solution is filtered, concentrated in vacuo and diluted with 15 ml of anhydrous toluene. The solution is refluxed for 1 hour at 90°.

The toluene solution is then concentrated in vacuo, placed under an argon atmosphere, diluted with a 25% solution of 0.1N HCl in THF and stirred for 18 hours. The reaction mixture is diluted with 50 ml of water and washed with 50 ml of ether. The aqueous solution is then neutralized with saturated NaHCO₃, extracted with two 100 ml portions of ethyl acetate, washed with brine and dried over anhydrous magnesium sulfate to provide the title amine.

C.
[1α,2β(5Z),3β,4α,5α,6α]-7-[5,6-Epoxy-3-(Heptylamino)-7-oxabicyclo[2.2.1]hept-2-yl]-3-heptenoic acid, methyl ester To 135 mg (0.51 mmole) of the title B amine in 3 ml of anhydrous methanol under an argon atmosphere at 25° is added 87.3 mg (0.76 mmole, 1.5 eq) of heptanal and ca. 300 mg of activated crushed 3 Å molecular sieves. This solution is stirred for 55 hours, diluted with 4 ml of anhydrous methanol, cooled to 0°, and an excess of sodium borohydride is added. This reaction is stirred for 30 minutes, quenched with 1 ml of acetone, diluted with 100 ml of ether and washed successively with 50 ml of water, and 50 ml of brine, and dried over anhydrous magnesium sulfate. This material is purified by preparative TLC on a 2 mm 20X20 Merck silica gel-60 F254 plate using 35/3.5/1-chloroform:methanol:88% formic acid as the eluent to provide the title ester as an oil.

D.
[1α,2β(5Z),3β,4α,5α,6α]-7-[5,6-Epoxy-3-(Heptylamino)-7-oxabicyclo[2.2.1]hept-2-yl]-5-heptenoic acid 112 mg (0.31 mmole) of the title C ester is diluted with 10 ml of 1N sodium hydroxide solution and refluxed at 95° for 45 minutes under an argon atmosphere. This solution is cooled, diluted with 10 ml of water and washed with 20 ml of ether. The aqueous layer is acidified to ca. pH 6.5 with dilute hydrochloric acid, extracted with two 100 ml portions of ethyl acetate and dried over anhydrous magnesium sulfate. This material is purified by flash chromatography on an LP-1 silica column using a 10% methanol in methylene chloride solution as the eluent, concentrated in vacuo, diluted with distilled methylene chloride and filtered through a millipore membrane to provide the title product.

EXAMPLE 8

[1α,2β(5Z),3β,4α,5α,6α]-7-[5,6-Epoxy-3-(Cyclopentylamino)methyl]-7-oxabicyclo[2.2.1]hept-2-yl]-5-heptenoic acid Following the procedure of Example 2 except substituting cyclopentylamine for hexylamine, the title compound is obtained.

EXAMPLE 9

[1α,2β(5Z),3β,4α,5α,6α]-7-[5,6-Epoxy-3-(Cyclohexylmethylamino)methyl]-7-oxabicyclo[2.2.1]hept-2-yl]-5-heptenoic acid Following the procedure of Example 2 except substituting cyclohexylmethylamine for hexylamine, the title compound is obtained.

EXAMPLE 10

(1α,2β,3β,4α,5α,6α-7-[5,6-Epoxy-3-(Pentylamino)methyl]-7-oxabicyclo[2.2.1]hept-2-yl]heptanoic acid Following the procedure of Example 3 except substituting pentylamine for hexylamine, the title compound is obtained.

EXAMPLE 11

[1α,2β(5Z),3β,4α,5α,6α]-7-[5,6-Epoxy-3-(Heptylamino)methyl]-7-oxabicyclo[2.2.1]hept-2-yl]-5-heptenoic acid Following the procedure of Example 2 except substituting heptylamine for hexylamine, the title compound is obtained.

EXAMPLE 12

1α,2β(5Z),3β,4α,5α,6α]-7-[5,6-Epoxy]-3-Cycloheptylamino)methyl]-7-oxabicyclo[2.2.1]hept-2-yl]-5-heptenoic acid Following the procedure of Example 2 except substituting cycloheptylamine for hexylamine, the title compound is obtained.

EXAMPLE 13

(1α,2β,3β,4α,5α,6α)-7-[5,6-Epoxy-3-(Heptylamino)methyl]-7-oxabicyclo[2.2.1]hept-2-yl]heptanoic acid Following the procedure of Example 3 except substituting heptylamine for hexylamine, the title compound is obtained.

EXAMPLE 14

[1α,2β(5Z),3β,4α,5α,6α]-7-[5,6-Epoxy-3-(Pentylamino)-7-oxabicyclo[2.2.1]hept-2-yl]-5-heptenoic acid Following the procedure of Example 7 except substituting pentanal for heptanal, the title compound is obtained.

EXAMPLE 15

[1α,2β(5Z),3β,4α,5α,6α]-7-[5,6-Epoxy-3-(Hexylamino)-7-oxabicyclo[2.2.1]hept-2-yl]-5-heptenoic acid Following the procedure of Example 7 except substituting hexanal for heptanal, the title compound is obtained.

EXAMPLE 16

(1α,2β,3β,4α,5α,6α)-7-[5,6-Epoxy-3-[[2-(1-Oxopentyl)-hydrazino]methyl]-7-oxabicyclo[2.2.1]hept-2-yl]heptanoic acid A. Pentanoyl hydrazine Methyl valerate (11.62 g, 0.1 mol) was added to hydrazine hydrate (5.0 g, 0.1 mol). The reaction was heated at reflux under vigorous stirring for 24 hours. Low boiling materials (MeOH and H₂O) were removed in vacuo and the residue was crystallized from isopropyl ether to give the title compound in the form of needle crystals (10.5 g, 0.0905 mol, 91%, m.p. 59°-61° C.).

B. (1α,2β,3β,4α,5α,6α)-7-[5,6-Epoxy-3-[[(1-Oxopentyl)-hydrazono]methyl]-7-oxabicyclo-[2.2.1]hept-2-yl]heptanoic acid, methyl ester Example 1 Part M aldehyde (564 mg, 2 mmol) and the title A hydrazide (255.2 mg, 2.2 mmol) are stirred in EtOH (10 ml) at room temperature for 1 hour. The reaction is poured into Et₂O (150 ml), which is washed with 1N HCl (30 ml×2), saturated NaHCO₃ (30 ml×2), brine (30 ml×2), and dried over MgSO₄. Filtration and evaporation of solvent give a viscous oil (739 mg), which is purified by silica gel column eluted with Et₂O/EtOAc-4/1 to give an oil. Upon standing, the oil solidifies. Crystallization from diisopropyl ether/pet ether affords title compound.

C.
(1α,2β,3β,4α,5α,6α)-7-[5,6-Epoxy-3-[[2-(1-Oxopentyl)-hydrazino]methyl-7-oxabicyclo[2.2.1]hept-2-yl]heptanoic acid, methyl ester NaBH₃CN (57 mg, 0.92 mmol) is added to a magnetically stirred solution of the title B compound (268 mg, 0.71 mmol) in MeOH (8.5 ml), followed by addition of AcOH (1.5 ml) dropwise. After 2¼ hours stirring at room temperature, additional NaBH₃CN (40 mg, 0.64 mmol) and AcOH (1 ml) are added. Stirring is continued at room temperature for 1 hour. Then, the reaction is quenched by addition of 2N HCl to pH 1 and stirred for 30 minutes. The reaction is basified by addition of saturated NaHCO₃. The products are extracted with Et₂O (100 ml×2). The combined ether layers are washed with brine and dried over MgSO₄. Filtration and evaporation of solvent gives the title compound which is purified by a silica gel column (silica 60, 15 g) eluted with ether/pet ether (1/1).

D.
(1α,2β,3β,4α,5α,6α)-7-[5,6-Epoxy-3-[[2-(1-Oxopentyl)-hydrazino]methyl]-7-oxabicyclo[2.2.1]hept-2-yl]heptanoic acid 1N LiOH (6 ml) is added to the title C ester (223 mg, 0.59 mmol) in THF (30 ml) and H₂O (6 ml) at room temperature. After 6 hours stirring at room temperature, the reaction is quenched by addition of 1N HCl (6 ml) and poured into brine (20 ml). The products are extracted with ether (100 ml×3). The combined ether layers are washed with brine (50 ml×3) and dried over Na₂SO₄. Filtration and evaporation of solvent yield a slightly yellow colored oil (210 mg), which is purified by a silica gel column (silica 60, 20g) eluted with CH₂Cl₂/MeOH (9.4/0.6) to give the title product.

EXAMPLE 17
[1α,2β(5Z),3β,4α,5α,6α]-7-[5,6-Epoxy-3-[[2-(1-Oxopentyl)hydrazino]methyl]-7-oxabicyclo[2.2.1]hept-2-yl]-5-heptenoic acid

A.
[1α,2β(5Z),3β,4α,5α,6α]-7-5,6-Epoxy-3-[[(1-Oxopentyl)hydrazono]methyl]-7-oxabicyclo[2.2.1]hept-2-yl]-5-heptenoic acid, methyl ester A solution of the Example 1M aldehyde (560 mg, 2 mmol) and pentanoyl hydrazide (prepared as described in Example 16, Part A) (255.1 mg, 2.2 mmol) in EtOH (10 ml) is stirred at room temperature for 2 hours. The reaction mixture is poured into 100 ml of ether and washed with 1N HCl (2×20 ml), saturated NaHCO₃ solution (2×20 ml) and saturated NaCl solution (2×20 ml). The ether solution is dried over MgSO₄, filtered and freed of solvent in vacuo leaving an oil. This is chromatographed on 30 g silica gel 60, eluting with ether to give the title compound.

B.
[1α,2β(5Z),3β,4α,5α,6α]-7-[5,6-Epoxy-3-[[2-(1-Oxopentyl)hydrazino]methyl]-7-oxabicyclo[2.2.1]hept-2-yl]-5-heptenoic acid, methyl ester Following the procedure of Example 16 Part C but substituting the above Part A hydrazono compound for the Example 16 title B compound, the above title B is obtained.

C.
[1α,2β(5Z),3β,4α,5α,6α]-7-[5,6-Epoxy-3-[[2-(1-Oxopentyl)hydrazino]methyl]-7-oxabicyclo[2.2.1]hept-2-yl]-5-heptenoic acid Following the procedure of Example 16 Part D but substituting the Part B methyl ester for the Example 16 Part C methyl ester, the title acid product is obtained.

EXAMPLE 18
[1α,2β(5Z),3β,4α,5α,6α]-7-[5,6-Epoxy-3-[[(Pentyloxy)amino]methyl]-7-oxabicyclo[2.2.1]hept-2-yl]-5-heptenoic acid

A. Ethyl N-hydroxyurethane

H₂N-OH.HCl (27.8 g, 0.40 mol) was added portionwise to a solution of Na₂CO₃ (62.4 gm, 0.59 mol) in H₂O (184 ml) under vigorous magnetic stirring. The reaction was endothermic and gave a white solid suspension. Then, ethyl chloroformate (42.4 g) was added dropwise at 0° C. in an ice bath. After completing the addition, the reaction was warmed to room temperature and stirring was continued for 1.5 hours. The reaction was acidified to pH 2 by addition of concentrated HCl. The products were extracted into Et₂O by a continuous liquid-liquid extractor (24 hours). The ether layer was dried over MgSO₄. Filtration and evaporation of solvent in vacuo yielded the title compound in the form of a clear yellow oil (37.3 g, 0.355 mol, 89%). The crude product was pure enough for a next reaction, so that no purification was attempted.

B. Ethyl O-pentyl-N-hydroxyurethane

KOH (6.6 g, 0.12 mol) dissolved in EtOH (30 ml) was added to 1-bromopentane (15.4 g, 0.1 mol) and ethyl N-hydroxyurethane (prepared as described in Part A, 10.5 g, 0.1 mol). The reaction was heated at reflux for 6 hours. The reaction was poured into ether (400 ml), and the resulting solids were filtered. The filtrate was washed with saturated NH₄Cl and dried over MgSO₄. Filtration and evaporation of solvents in vacuo gave a colorless liquid (14.3 g) which was distilled to afford the title compound in the form of a colorless oil (10.6 g, 0.061 mol, b.p. 91° C./2.75 mHg, 61%).

C. O-pentylhydroxyamino hydrochloride

Ethyl O-pentyl-N-hydroxyurethane, prepared as described in Part B, (10.6 g, 0.061 mol) and KOH (13.6 g, 0.242 mol) in H₂O (65 ml) were heated at reflux for 4 hours. The products were extracted into ether (150 ml×3). The combined ether layers were washed with 2N HCl (100 ml). Then, the water layer was washed with Et₂O (100 ml) and evaporated off in vacuo to give white solid (6.8 g). MeOH (50 ml) was added to dissolve most of the solid. Undissolved solid was removed by filtration and the filtrate was evaporated in vacuo to give the title compound in the form of a white solid (6.5 g, 46 mmol, 77%).

D.
[1α,2β(5Z),3β,4α,5α,6α]-7-[5,6-Epoxy-3-[[(Pentyloxy)imino]methyl]-7-oxabicyclo[2.2.1]hept-2-yl]-5-heptenoic acid, methyl ester O-pentylhydroxyamino hydrochloride (306.9 mg, 2.2 mmol) is added to a suspension of NaOAc (196.8 mg, 2.4 mmol) in dry EtOH (10 ml). NaCl is immediately precipitated out. Then, aldehyde prepared as described in Example 1, Part M (560 mg, 2.0 mmol) in dry EtOH (1 ml) is added at room temperature. After 1 hour stirring, the reaction mixture is poured into Et$_2$O, which is washed with 1N HCl (20 ml×2), saturated NaHCO$_3$ (20 ml×2), brine (20 ml×2) and dried over MgSO$_4$. Filtration and evaporation of solvents in vacuo gives an oil which is purified by column chromatography (silica 60, 30 g) and eluted with ether/pet. ether (1:2) to give the title compound.

E.

[1α,2β(5Z),3β,4α,5α,6α]-7-[5,6-Epoxy-3-[[(Pentyloxy)amino]methyl]-7-oxabicyclo[2.2.1]hept-2-yl]-5-heptenoic acid, methyl ester NaBH$_3$CN (57 mg, 0.92 mmol) is added to a magnetically stirred solution of Part D oxime (258 mg, 0.71 mmol) in MeOH (8.5 ml), followed by addition of AcOH (1.5 ml) dropwise. After 2¼ hours stirring at room temperature, additional NaBH$_3$CN (40 mg, 0.64 mmol) and AcOH (1 ml) are added. Stirring is continued at room temperature for 1 hour. Then, the reaction is quenched by addition of 2N HCl to pH 1 and stirred for 30 minutes. The reaction is basified by addition of saturated NaHCO$_3$. The products are extracted with Et$_2$O (100 ml×2). The combined ether layers are washed with brine and dried over MgSO$_4$. Filtration and evaporation of solvent gives the title compound.

F.

[1α,2β(5Z),3β,4α,5α,6α]-7-[5,6-Epoxy-3-[[(Pentyloxy)amino]methyl]-7-oxabicyclo[2.2.1]hept-2-yl]-5-heptenoic acid 1N LiOH (6 ml) is added to the title E ester (215 mg, 0.59 mmol) in THF (30 ml) and H$_2$O (6 ml) at room temperature. After 6 hours stirring at room temperature, the reaction is quenched by addition of 1N HCl (6 ml) and poured into brine (20 ml). The products are extracted with ether (100 ml×3). The combined ether layers are washed with brine (50 ml×3) and dried over Na$_2$SO$_4$. Filtration and evaporation of solvent yield an oil which is purified by a silica gel column (silica 60, 20 g) eluted with CH$_2$Cl$_2$/MeOH (9.4/0.6) to give the title product.

EXAMPLE 19

[1α,2β(5Z),3β,4α,5α,6α]-7-[5,6-Epoxy-3-[[2-(Propoxycarbonyl)hydrazino]methyl]-7-oxabicyclo[2.2.1]hept-2-yl]-5-heptenoic acid

A.

[1α,2β(5Z),3β,4α,5α,6α]-7-[5,6-Epoxy-3-[[(Propoxycarbonyl)hydrazono]methyl]-7-oxabicyclo[2.2.1]hept-2-yl]-5-heptenoic acid, methyl ester

[1α,2β(5Z),3β,4α,5α,6α]-7-[3-Formyl-7-oxabicyclo[2.2.1]hept-2-yl]-5-heptenoic acid, methyl ester, prepared as described in Example 1, part M, (560 mg, 2 mmol) and n-propyl hydrazinocarboxylate (prepared by refluxing hydrazine hydrate (1.9 g, 0.038 mmol) and di-n-propyl carbonate (5.3 g, 0.036 mol) for 43 hours), 283.2 mg, 2.4 mmol, are dissolved in EtOH (10 ml) and the reaction is stirred for 2 hours at room temperature. The reaction is concentrated in vacuo leaving a colorless oil (672 mg), which is purified by silica gel column (silica 60, 30 g) eluted with Et$_2$O/pet. ether (3.5/1.5) to give a colorless oil.

B.

[1α,2β(5Z),3β,4α,5α,6α]-7-[5,6-Epoxy-3-[[2-(Propoxycarbonyl)hydrazino]methyl]-7-oxabicyclo[2.2.1]hept-2-yl]-5-heptenoic acid, methyl ester Title A compound (347 mg, 0.96 mmol) is dissolved in methanol (9 ml) and sodium cyanoborohydride (90 mg, 1.43 mmol) is added. Glacial acetic acid (4.5 ml) is then added dropwise in 2 minutes. The mixture is stirred at room temperature for 2.5 hours and then acidified to pH 1 with 1N HCl solution. After stirring at room temperature for 30 minutes, the mixture is basified with NaHCO$_3$. The product is extracted into ether (3×60 ml) and washed with saturated NaHCO$_3$ solution (50 ml) and saturated NaCl solution (50 ml), dried (MgSO$_4$) and freed of solvent in vacuo leaving an oil. This is chromatographed on silica gel 60 (20 g) to give the title compound as an oil.

C.

[1α,2β(5Z),3β,4α,5α,6α]-7-[5,6-Epoxy-3-[[2-(Propoxycarbonyl)hydrazino]methyl]-7-oxabicyclo[2.2.1]hept-2-yl]-5-heptenoic acid The title B methyl ester (280 mg, 0.77 mmol) is dissolved in THF (40 ml) and water (7 ml) in an argon atmosphere. While stirring, 1N LiOH solution (7.7 ml) is added and the mixture is stirred at room temperature 4 hours. 1N HCl solution (7.7 ml) is added to adjust the pH to ~6 and the mixture is poured into saturated NaCl column (200 ml). The product is extracted into ethyl acetate (3×100 ml). The combined ethyl acetate extracts are washed with saturated NaCl solution (4×75 ml), dried (MgSO$_4$) and freed of solvent in vacuo leaving an oil. This is chromatographed silicar CC7 (25 g), eluting with 2% MeOH in CH$_2$Cl$_2$ to give the title product.

EXAMPLE 20

[1α,2β(5Z),3β,4α,5α,6α]-7-[5,6-Epoxy-3-[(Phenylamino)methyl]-7-oxabicyclo[2.2.1]hept-2-yl]-5-heptenoic acid Following the procedure of Example 2 except substituting aniline for hexylamine, the title product is obtained.

EXAMPLE 21

[1α,2β(5Z),3β,4α,5α,6α]-7-[5,6-Epoxy-3-(Benzylamino)-7-oxabicyclo[2.2.1]hept-2-yl]-5-heptenoic acid Following the procedure of Example 7 except substituting benzaldehyde for heptanal, the title compound is obtained.

EXAMPLE 22

[1α,2β(5Z),3β,4α,5α,6α]-7-[5,6-Epoxy-3-[(Benzylamino)methyl]-7-oxabicyclo[2.2.1]hept-2-yl]-5-heptenoic acid Following the procedure of Example 2 except substituting benzylamine for hexylamine, the title product is obtained.

EXAMPLE 23

[1α,2β,3β,4α,5α,6α)-7-[5,6-Epoxy-3-[(benzylamino)-methyl-7-oxabicyclo[2.2.1]hept-2-yl]heptanoic acid Following the procedure of Examples 3 and 2 except substituting benzylamine for hexylamine, the title product is obtained.

EXAMPLE 24

[1α,2β(5Z),3β,4α,5α,6α]-7-[5,6-Epoxy-3-(Phenethylamino)-7-oxabicyclo[2.2.1]hept-2-yl]-5heptenoic acid Following the procedure of Example 7 except substituting phenylacetaldehyde for heptanal, the title compound is obtained.

EXAMPLE 25

(1α,2β,3β,4α,5α,6α)-7-[5,6-Epoxy-3-[[2-(Phenylcarbonyl)hydrazino]methyl]-7-oxabicyclo[2.2.1]hept-2-yl]heptanoic acid Following the procedure of Example 16 except substituting benzoyl hydrazine for pentanoyl hydrazine, the title product is obtained.

EXAMPLE 26

[1α,2β(5Z),3β,4α,5α,6α]-7-[5,6-Epoxy-3-[[2-(Phenylcarbonyl)hydrazino]methyl]-7-oxabicyclo[2.2.1]hept-2-yl]-5-heptenoic acid Following the procedure of Example 17 except substituting benzoyl hydrazine for pentanoyl hydrazine, the title product is obtained.

EXAMPLE 27

(1α,2β,3β,4α,5α,6α)-7-[5,6-Epoxy-3-[[2-(Benzylcarbonyl)hydrazino]methyl]-7-oxabicyclo[2.2.1]hept-2-yl]heptanoic acid Following the procedure of Example 16 except substituting phenylacetyl hydrazine for pentanoyl hydrazine, the title compound is obtained.

EXAMPLE 28

[1α,2β(5Z),3β,4α,5α,6α]-7-[5,6-Epoxy-3-[[2-(Benzylcarbonyl)hydrazino]methyl]-7-oxabicyclo[2.2.1]hept-2-yl]-5-heptenoic acid Following the procedure of Example 17 except substituting phenylacetyl hydrazine for pentanoyl hydrazine, the title compound is obtained.

EXAMPLE 29

(1α,2β,3β,4α,5α,6α)-7-[5,6-Epoxy-3-[[2-Phenoxycarbonyl)hydrazino]methyl]-7-oxabicyclo[2.2.1]hept-2-yl]heptanoic acid Following the procedure of Example 16 except substituting phenoxycarbonyl hydrazine for pentanoyl hydrazine, the title compound is obtained.

EXAMPLE 30

[1α,2β(5Z),3β,4α,5α,6α]-7-[5,6-Epoxy-3-[[2-(Phenoxycarbonyl)hydrazino]methyl]-7-oxabicyclo[2.2.1]hept-2-yl]-5-heptenoic acid Following the procedure of Example 17 except substituting phenoxycarbonyl hydrazine for pentanoyl hydrazine, the title compound is obtained.

EXAMPLE 31

(1α,2β,3β,4α,5α,6α)-7-[5,6-Epoxy-3-[[2-(Benzyloxycarbonyl)hydrazino]methyl]-7-oxabicyclo[2.2.1]hept-2-yl]heptanoic acid Following the procedure of Example 16 except substituting benzyloxycarbonyl hydrazine for pentanoyl hydrazine, the title product is obtained.

EXAMPLE 32

[1α,2β(5Z),3β,4α,5α,6α]-7-[5,6-Epoxy-3-[[2-(Benzyloxycarbonyl)hydrazino]methyl]-7-oxabicyclo[2.2.1]hept-2-yl]-5-heptenoic acid Following the procedure of Example 17 except substituting benzyloxycarbonyl hydrazine for pentanoyl hydrazine, the title compound is obtained.

EXAMPLE 33

(1α,2β,3β,4α,5α,6α)-7-[5,6-Epoxy-3-[[2-(Phenylalanyl)hydrazino]methyl]-7-oxabicyclo[2.2.1-]hept-2-yl]heptanoic acid Following the procedure of Example 16 except substituting phenylalaninyl hydrazine for pentanoyl hydrazine, the title product is obtained.

EXAMPLE 34

[1α,2β(5Z),3β,4α,5α,6α]-7-[5,6-Epoxy-3-[[2-(Phenylalanyl)hydrazino]methyl]-7-oxabicyclo[2.2.1-]hept-2-yl]-5-heptenoic acid Following the procedure of Example 17 except substituting phenylalaninyl hydrazine for pentanoyl hydrazine, the title compound is obtained.

EXAMPLE 35

(1α,2β,3β,4α,5α,6α)-7-[5,6-Epoxy-3-[[2-(Phenylaminocarbonyl)hydrazino]methyl]-7-oxabicyclo[2.2.1]hept-2-yl]heptanoic acid Following the procedure of Example 16 except substituting 4-phenylsemicarbazide for pentanoyl hydrazine, the title compound is obtained.

EXAMPLE 36

(1α,2β,3β,4α,5α,6α)-7-[5,6-Epoxy-3-[[2-(Propylaminocarbonyl)hydrazino]methyl]-7-oxabicyclo[2.2.1]hept-2-yl]heptanoic acid Following the procedure of Example 16 except substituting 4-propylsemicarbazide for pentanoyl hydrazine, the title product is obtained.

EXAMPLE 37

[1α,2β(5Z),3β,4α,5α,6α]-7-[5,6-Epoxy-3-[[2-(Propylaminocarbonyl)methyl]-7-oxabicyclo[2.2.1-]hept-2-yl]-5-heptenoic acid Following the procedure of Example 17 except substituting 4-propylsemicarbazide for pentanoyl hydrazine, the title compound is obtained.

EXAMPLE 38

[1α,2β(5Z),3β,4α,5α,6α]-7-[5,6-Epoxy-3-[(2-hexylamino)ethyl]-7-oxabicyclo[2.2.1]hept-2-yl]-5-heptenoic acid

A.

[1α,2β(5Z),3β,4α,5α,6α]-7-5,6-Epoxy-3-(2-Oxoethyl)-7-oxabicyclo[2.2.1]hept-2-yl]-5-heptenoic acid, methyl ester Into a dry 1000 ml round bottom 3-necked flask containing a stir bar was added dried 2.9 g (37.7 mmoles) methoxymethyltriphenylphosphonium chloride ($(C_6H_5)_3P^+-CH_2OCH_3Cl^-$) and 235 ml distilled toluene (stored over molecular sieves). The resulting suspension was stirred in an ice bath, under argon, until cold and then a 1.55M solution of 18.3 ml (28.3 mmol) of potassium t-amylate in toluene was added dropwise. A bright red solution formed which was stirred at 0° C. for an additional 35 minutes. Thereafter, a solution of 4.97 g (18.8 mmol) [1α,2β(5Z),3β,4α,5α,6α]-7-[5,6-epoxy-3-formyl-7-oxabicyclo[2.2.1]hept-2-yl]-5-heptenoic acid, methyl ester in 60 ml toluene is added by means of a dropping funnel over a 35 minute period with the ice-bath still in place. The reaction is then quenched by addition of 2.3 g (39 mmol) acetic acid in 5 ml ether. The reaction mixture was imemdiately poured into 200 ml saturated NH₄Cl and extracted with ether (4×200 ml). The combined ether phases are washed with NaCl, saturated solution, and dried (MgSO₄) and concentrated to yield title compound.

B. [1α,2β(5Z), 3β,4α,5α,6α]-7-[5,6-Epoxy-3-[(2-(hexylamino)ethyl]-7-oxabicyclo[2.2.1]hept-2-yl]-5-heptenoic acid Following the procedure of Example 2 except substituting the part A aldehyde for the Example 1, Part M aldehyde, the title compound is obtained.

EXAMPLE 39

[1α,2β(5Z), 3β,4α,5α,6α]-7-[5,6-Epoxy-3-(4-hexylamino)butyl]-7-oxabicyclo[2.2.1]hept-2-yl]-5-heptenoic acid

A. 1α,2β(5Z), 3β,4α,5α,6α]-7-[5,6-Epoxy-3-(4-Oxo)butyl-7-oxabicyclo[2.2.1]hept-2-yl]-5-heptenoic acid, methyl ester

[1α,2β(5Z), 3β,4α,5α,6α]-7-[5,6-Epoxy-3-(2-oxoethyl)-7-oxabicyclo[2.2.1]hept-2-yl]-5-heptenoic acid, methyl ester is treated with methoxymethyltriphenylphosphonium chloride and potassium t-amylate employing the procedure described in Example 38. The product of this reaction is treated with aqueous trifluoroacetic acid to give [1α,2β(5Z), 3β,4α,5α,6α]-7-[5,6-epoxy-[3-(3-oxo)propyl-7-oxabicyclo[2.2.1]hept-2-yl]]-5-heptenoic acid, methyl ester. The compound is treated with methoxymethyltriphenylphosphonium chloride and potassium t-amylate employing the procedure described in Example 39. The product of the latter reaction is treated with aqueous trifluoroacetic acid to give the title A compound.

B. [1α,2β(5Z), 3β,4α,5α,6α]-7-[5,6-Epoxy-3-[(4-hexylamino)butyl]-7-oxabicyclo[2.2.1]hept-2-yl]-5-heptenoic acid Following the procedure of Example 2 except substituting the Part A aldehyde for the Example 1 part M aldehyde, the title compound is obtained.

It will also be appreciated that the carboxybutyl triphenylphosphonium bromide of the structure

$Br(C_6H_5)_3P(CH_2)_3-COOH$ employed in forming the upper side chain in the aforementioned examples may be replaced by

$Br(C_6H_5)_3P(CH_2)_m COOR$ wherein $(CH_2)_m$ is defined hereinbefore, to form compounds of the invention wherein the upper side chain is of the structure

$-CH_2-A-(CH_2)_m-COOR$ wherein m is 1, 2, 4 or 5.

What is claimed is:
1. A compound having the formula

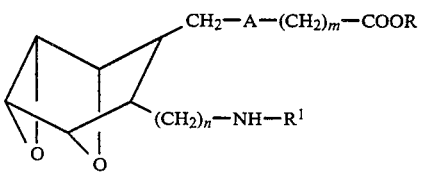

and including all stereoisomers thereof;
wherein A is CH=CH or $(CH_2)_2$;
m is 1 to 8; n is 0 to 5; R is H, lower alkyl, alkali metal or polyhydroxylamine salt; and $R^1$ is lower alkyl, aryl, aryl-lower alkyl, cycloalkyl, cycloalkylalkyl, lower alkenyl containing 2 to 12 carbons, lower alkoxy, aryl-lower alkoxy or

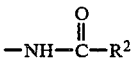
$$-NH-\overset{O}{\underset{\|}{C}}-R^2$$

wherein $R^2$ is loweralkyl, lower alkoxy, aryl, aryl-lower alkyl, aryloxy, aryl-lower alkoxy, lower alkylamino, arylamino or aryl-lower alkylamino wherein lower alkyl or alkyl alone or as part of another group contains 1 to 12 carbons and is unsubstituted or is substituted with halo, CF₃, alkoxy, aryl, alkyl-aryl, haloaryl, cycloalkyl, alkylcycloalkyl, hydroxy, alkylamino or alkylthio;
aryl alone or as part of another group is phenyl or naphthyl optionally substituted with 1 or 2 lower alkyl groups, 1 or 2 halogens, 1 or 2 hydroxy groups, 1 or 2 lower alkoxy groups, 1 or 2 alkylthio groups or 1 or 2 alkylamino groups and wherein phenyl may also be independently substituted with a thiol, amino or

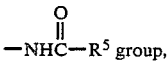
$$-NH\overset{O}{\underset{\|}{C}}-R^5 \text{ group,}$$

wherein $R^5$ is H or lower alkyl;
cycloalkyl alone or as part of another group contains 3 to 12 carbons and is unsubstituted or is substituted with 1 or 2 halogens, 1 or 2 lower alkyl groups and/or 1 or 2 lower alkoxy groups, an aryl group, 1 or 2 hydroxyl groups, 1 or 2 alkylamino groups, or 1 or 2 alkylthio groups; and
$(CH_2)_m$ and $(CH_2)_n$ include straight or branched chain radicals having from 1 to 8 carbons in the normal chain in the case of $(CH_2)_m$ and having 1 to 5 carbons in the normal chain in the case of $(CH_2)_n$ and may contain 1 or 2 lower alkyl substitutents.

2. The compound as defined in claim 1 wherein the term "aryl" when defining an $R^1$ and/or $R^2$ substituent or when present as part of an $R^1$ and/or $R^2$ substituent may be the same or different and is defined as phenyl, naphthyl, phenyl substituted with 1 or 2 lower alkyl groups, 1 or 2 halogens, 1 or 2 lower alkoxy groups, 1 or 2 hydroxy groups, or

or naphthyl substituted with 1 or 2 lower alkyl groups, 1 or 2 halogen groups or, 1 or 2 lower alkoxy groups.

3. The compound as defined in claim 1 having the formula

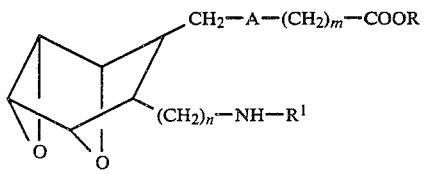

wherein $R^1$ is lower alkyl, lower alkoxy, aryl-lower alkoxy or

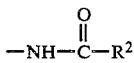

including all stereoisomers thereof.

4. The compound as defined in claim 2 wherein A is CH=CH.

5. The compound as defined in claim 3 wherein $R^1$ is

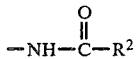

and $R^2$ is phenylamino including all stereoisomers thereof.

6. The compound as defined in claim 3 wherein $R^1$ is pentyl, hexyl or heptyl.

7. The compound as defined in claim 1 having the [1α,2β(5Z), 3β,4α,5α,6α]-7-[5,6-Epoxy-3-[[2-[(phenylamino)carbonyl]hydrazino]methyl]-7-oxabicyclo[2.2.1]hept-2-yl]-5-heptenoic acid or the methyl ester thereof or all stereoisomers thereof.

8. A method of inhibiting arachidonic acid-induced platelet aggregation and bronchoconstriction, which comprises administering to the circulatory system of a mammalian host an effective amount of a compound as defined in claim 1 or a pharmaceutically acceptable salt thereof.

9. The method as defined in claim 8 wherein said compound is administered in an amount within the range of from about 1 to about 100 mg/kg.

10. A composition for inhibiting arachidonic acid-induced plately aggregation and bronchoconstriction comprising an effective amount of a compound as defined in claim 1 or a pharmaceutically acceptable salt thereof, and a pharmaceutically acceptable carrier thereof.

11. A method of inhibiting bronchoconstriction associated with asthma, which comprises administering to a mammalian host an effective amount of a compound as defined in claim 1 or a pharmaceutically acceptable salt thereof.

12. A method for treating peripheral vascular disease, which comprises topically or systemically administering to a mammalian host an effective amount of a compound as defined in claim 1 or a pharmaceutically acceptable salt thereof.

* * * * *